United States Patent [19]

Schneider et al.

[11] Patent Number: 5,356,636
[45] Date of Patent: Oct. 18, 1994

[54] STABLE VITAMIN AND/OR CAROTENOID PRODUCTS IN POWDER FORM, AND THE PREPARATION THEREOF

[75] Inventors: Joachim U. Schneider, Weisenheim; Horst Schumacher, Bobenheim; Wolfgang Bewert, Frankenthal; Guenter Gaus, Biblis; Udo Rheude, Otterstadt, all of Fed. Rep. of Germany

[73] Assignee: BASF Aktiengesellschaft, Ludwigshafen, Fed. Rep. of Germany

[21] Appl. No.: 991,318

[22] Filed: Dec. 16, 1992

[30] Foreign Application Priority Data

Dec. 14, 1991 [DE] Fed. Rep. of Germany ....... 4141351

[51] Int. Cl.$^5$ ................................................ A61K 9/14
[52] U.S. Cl. .................... 424/489; 424/499; 424/500
[58] Field of Search ............... 424/489; 435/840; 514/167; 530/354

[56] References Cited

U.S. PATENT DOCUMENTS

| | | | |
|---|---|---|---|
| 4,590,161 | 5/1986 | Kula et al. | 435/840 |
| 4,844,934 | 7/1989 | Lueddecke et al. | 514/772 |
| 4,863,950 | 9/1989 | Morganti | 415/419 |
| 4,892,889 | 1/1990 | Kirk et al. | 514/167 |
| 5,153,177 | 10/1992 | Chaundy et al. | 530/354 |

FOREIGN PATENT DOCUMENTS 140255  5/1985  European Pat. Off. .
285682  6/1987  European Pat. Off. .
993138  11/1961  United Kingdom .

OTHER PUBLICATIONS

R. A. Morton, Fat–Soluble Vitamins, International Encyclopaedia of Food and Nutrition, vol. 9, Pergamon Press Ltd., 1970, pp. 129 et seq.

Primary Examiner—John Kight, III
Assistant Examiner—William E. Benston, Jr.
Attorney, Agent, or Firm—Keil & Weinkauf

[57] ABSTRACT

A process for preparing stable dry powders which are insoluble in hot water and which contain fat-soluble vitamins and/or carotenoids, which comprises the following steps:
 a) preparing an aqueous dispersion containing essentially these fat-soluble active substances, film-forming colloids and reducing sugars,
 b) converting this dispersion into dry vitamin and/or carotenoid products in powder form and
 c) thermally curing the powder at from 60° to 180° C., wherein gelatin in combination with one or more organic amino compounds which are free or bonded in the manner of a salt and which contain a basic primary amino group and, in addition, either another amino group, a hydroxyl group, an alkoxy group or a carboxyl group, and/or in combination with sufficient basic alkali metal or alkaline earth metal compound for the dispersion to have a pH of from 7.5 to 10, is used as film-forming colloid, and the dry powders obtainable via this process are described.

6 Claims, No Drawings

STABLE VITAMIN AND/OR CAROTENOID PRODUCTS IN POWDER FORM, AND THE PREPARATION THEREOF

The present invention relates to stable dry powders which are insoluble in hot water and in which one or more fat-soluble vitamins and/or one or more carotenoids are embedded in a gelatin-based matrix, obtainable by a) preparing a dispersion containing essentially these fat-soluble active substances, reducing sugars and, as film-forming colloid, gelatin in amounts of from 20 to 35, preferably 24 to 34, in particular 25 to 30, % of the weight of the powder dry matter, in combination with one or more physiologically tolerated organic amino compounds which contain a basic primary amino group and, in addition, either another amino group, a hydroxyl group, an alkoxy group or a carboxyl group, in free form or in a form bonded in the manner of a salt, and/or in combination with sufficient basic alkali metal or alkaline earth metal compound for the dispersion to have a pH of from 7.5 to 10, preferably 8 to 9.5, b) converting this dispersion into dry vitamin and/or carotenoid products in powder form and c) thermally curing the powder at from 60° to 180° C., preferably 70° to 130° C., and to a process for the preparation thereof.

Vitamin and carotenoid products in powder form are generally known and are used in large quantities in the pharmaceutical industry and in the food and animal feed industries. Thus, many processes for preparing suitable products are described in the literature.

Conventionally, the fat-soluble vitamins and/or carotenoids are dispersed in an aqueous solution of an organic film-forming colloid and the resulting dispersion is finally converted into dry products in powder form.

Gelatin is conventionally used in the prior art as film-forming colloid. Reasons which may be mentioned for preferring gelatin are:

1) gelatin is an excellent dispersion-stabilizing and film-forming agent;
2) gelatin forms thermoreversible gels, which means that it is industrially possible with suitable processes to dry the droplets or beadlets of the dispersion and thus obtain particles of optimal size;
3) gelatin is a good protective colloid and, in combination with antioxidants, has a stabilizing effect, i.e. the protective film is particularly impermeable to oxygen, which is particularly important for the fat-soluble vitamins which are particularly sensitive to oxygen (cf. R. A. Morton in Fat-soluble Vitamins, International Encyclopaedia of Food and Nutrition, Vol. 9, Pergamon Press Ltd., 1970, pp. 129 et seq.).

The stability of such products must meet particularly stringent requirements when they are to be used as additives to foodstuffs or to animal feeds, because when used for these they are often exposed to influences such as elevated temperatures, moisture, mechanical friction or pressure which are extremely damaging for the sensitive vitamins and carotenoids. This is why there has been no lack of attempts to develop processes which provide products with particular thermal and mechanical stability.

Thus, for example, GB 993 138 discloses the stabilization of certain vitamin products which contain gelatin as matrix by the particles being treated with a gelatin-denaturing agent such as formaldehyde, glyoxal, acetaldehyde or dihydroxyacetone, and subsequently heated, or else subjected only to a heat treatment.

The recently published Patent EP-B1 285 682 discloses a process for preparing spherical products which contain fat-soluble vitamins by emulsion formation using water, gelatin and a sugar, converting the emulsion into droplets, collecting the droplets in a mass of starch powder in such a way that the droplets remain separated from one another until their shape has been permanently formed, separating the resulting particles from excess starch powder and subsequently heating at from 90° to 180° C. The disadvantage of the process, which is intrinsically quite good, is that relatively large amounts of gelatin (from 35 to 45% of the weight of the dry matter) are required to prepare the products, which makes industrial preparation of the products uneconomic in view of the costs of the materials used and the process.

It is an object of the present invention to prepare vitamin and/or carotenoid products in powder form which have a lower content of costly gelatin but at least equivalent stability to hydrothermal and mechanical stress and are thus more suitable for producing, for example, premixes, pellets and extrudates for animal feed, and tablets for the drug sector.

We have found that this object is achieved by a process by which the above-defined stable dry powders which are insoluble in hot water and which contain one or more fat-soluble vitamins and/or one or more carotenoids can be obtained and which comprises the following steps:

a) preparing an aqueous dispersion containing essentially these fat-soluble active substances, film-forming colloids and reducing sugars, b) converting this dispersion into dry vitamin and/or carotenoid products in powder form, preferably by spraying into a cloud composed of a gas and hydrophobic silica, and c) thermally curing the powder at from 60° to 180° C., wherein gelatin in amounts of from 20 to 35% of the weight of the powder dry matter, in combination with one or more physiologically tolerated organic amino compounds which are free or bonded in the manner of a salt and which contain a basic primary amino group and, in addition, either another amino group, a hydroxyl group, an alkoxy group or a carboxyl group, which is free or bonded in the manner of a salt and/or in combination with sufficient basic alkali metal or alkaline earth metal compound for the dispersion to have a pH of from 7.5 to 10, is used as film-forming colloid.

The process according to the invention is advantageously carried out in such a way that the gelatin is used in amounts of from 24 to 34%, in particular 25 to 30%, of the weight of the powder dry matter, in combination with from 0.3 to 20% by weight, preferably 0.5 to 10% by weight, based on the powder dry matter, of amino compound which is free or bonded in the manner of a salt, the total of the amount of gelatin and the amount of amino compound not exceeding 45% by weight, preferably 40% by weight, in particular 35% by weight.

Although the use of amino acids and reducing sugars for preparing formulations in powder form of fat-soluble vitamins and the drying thereof on exposure to heat is described in JA-B 45-38348 (published 1970), this describes only vitamin powders based on alkali metal salts of casein, but not on gelatin. However, since casein, in contrast to gelatin, does not form thermo-reversible gels it is only possible in this way to obtain very fine-particle products which are not very suitable, for example, for use under hydrothermal stress because they are dispersible in water.

By contrast, the products in powder form produced according to the invention have excellent stability and insolubility in hot water. These properties are even evident in comparison with powders which have a high gelatin content but no amino compounds and are particularly important for use in animal feeds because in these the vitamin- and carotenoid-containing powders are exposed to chemical, mechanical and/or hydrothermal stress in premixes and during processing to pellets, extrudates or tablets. It should also be mentioned that the bioavailability of the active substances enclosed in the powders obtained according to the invention is completely retained.

The amino compounds can also according to the invention be used together with a basic alkali metal or alkaline earth metal compound such as an alkali metal or an alkaline earth metal hydroxide, an alkaline earth metal oxide or an alkaline earth metal or alkali metal carbonate. However, it is also possible for the basic compounds to be used in place of the amino compounds. When basic compounds are used it is most expedient for the process to be such that the dispersion has a pH of from 7.5 to 10, preferably 8 to 9.5, in particular 8 to 9, after addition of the basic compound.

The thermal treatment of the initially obtained powder results in the gelatin content being denatured owing to reaction of its free amino groups with the reducing sugars (Maillard reaction) and thus becoming insoluble in water. This effect is synergistically enhanced by the presence of the amino compounds described above, especially amino carboxylic acids, which assist crosslinking of the matrix by polymer formation. This means that part of the gelatin, which would be necessary in the prior art processes can be replaced by in each case considerably smaller amounts of the amino compounds described. When basic compounds are added there is presumably activation of the amino groups of a gelatin, which might explain why this also makes it possible to reduce the amount of gelatin required. Another advantage of the process according to the invention is that the customary crosslinking temperatures are reduced in the presence of the amino compounds and/or the basic compounds, i.e. crosslinking is possible at 60° C. or above, while the crosslinking temperatures required according to EP 285 682 are from 90° to 180° C., preferably 105° to 150° C. It is thus possible in the process according to the invention to reduce the thermal stress of the active substances during preparation compared with the process of EP 285 682.

The fat-soluble vitamins include vitamins A, E, D and K as well as mixtures thereof. For the purpose of the present invention they can be employed in the form of vitamin solutions in oils, as provitamins and as pure vitamins of natural or synthetic origin. Particularly interesting products contain vitamin A and its derivatives, especially vitamin A acetate, vitamin A palmitate and vitamin A propionate, and mixtures thereof.

By carotenoids are meant compounds such as β-carotene, ethyl apo-8'-carotenoate, apo-8'-catorenal, ci-tranaxanthin, canthaxanthin, zeaxanthin, astaxanthin, lutein, capsanthin and mixtures thereof.

The contents of vitamins or carotenoids are generally from about 5 to 50%, preferably 10 to 35%, of the weight of the powder dry matter.

The dispersion can be prepared in the process according to the invention using gelatin of the A or B type in a wide Bloom range. It is particularly advantageous to use gelatin with a Bloom value of from about 50 to about 250.

The dispersion can be prepared using all reducing sugars or sugar syrups containing reducing sugars. Reducing sugars include fructose, glucose, lactose, maltose, xylose, arabinose, ribose and invert sugar (glucose+fructose), honey, fructose syrups and glucose syrups. The sugars are generally used in amounts of from about 3 to 25% of the weight of the dry matter.

Suitable organic amino compounds which contain a basic primary amino group and, in addition, either another amino group, a hydroxyl group, an alkoxy group or a carboxyl group are thus aliphatic diamines such as ethylenediamine or hexamethylenediamine, alkanolamines such as ethanolamine, propanolamine or butanolamine, amino ethers such as 2-methoxyethylamine or 3-methoxypropylamine, or amino carboxylic acids in free form or in a form bonded in the manner of a salt. The use of amino carboxylic acids or of their salts has particular significance.

Suitable amino carboxylic acids are all natural and synthetic amino acids in their L form, D form or as racemate. The amino carboxylic acids can be α-, β- or ω-amino carboxylic acids in free form or in the form of salt-like compounds with acids or bases. Examples are glycine, α-alanine, β-alanine, valine, γ-aminobutyric acid, leucine, isoleucine, tyrosine, serine, methionine, arginine, phenylalanine, tryptophan or lysine, or else salts of the said amino acids.

It is of course also possible to use as amino carboxylic acid component mixtures of amino carboxylic acids which are free or in salt form, such as protein hydrolysates.

It is particularly advantageous to use readily accessible and thus low-cost amino carboxylic acids or their salts, such as lysine hydrochloride or calcium β-alaninate, especially calcium β-alaninate.

The amino compounds are generally used in amounts of from about 0.3 to 20%, preferably 0.5 to 10%, of the weight of the powder dry matter.

The gelatin is used according to the invention in amounts of from 20 to 35%, preferably 24 to 34%, in particular 20 to 30%, of the weight of the powder dry matter.

The dry powders according to the invention and their preparation have advantages over the known products when the total of the amount of gelatin and the amount of the organic amino compound does not exceed 45% by weight, preferably 40% by weight, in particular 35% by weight.

In addition to the obligatory ingredients, it is advantageous to add to the dispersion other compounds customary in the preparation of active substance dry powders.

It is particularly important when the dry powders are used as animal feed additives in the case of active substances which are sensitive to oxidation to add antioxidants such as ethoxyquin, butylated hydroxytoluene (BHT), butylated hydroxyanisole (BHA) or tocopherol, and stabilizers such as citric acid, phosphoric acid or phytic acid and their alkali metal or alkaline earth metal salts, or else complexing agents such as ethylenediaminetetraacetic acid (EDTA) or nitrilotriacetic acid (NTA).

However, the emulsion frequently also contains added humectants such as glycerol, sorbitol or polyethylene glycols or else additional emulsifiers such as lecithin.

In addition, additives such as starch, especially corn starch or maltodextrin, or thickeners such as gum arabic, guar gum, alginates and certain degraded starches, have proven useful for adjusting the viscosity of the emulsion.

For details of the importance, nature and amount of such additives, reference may be made to the relevant literature, for example to the abovementioned monograph entitled Fat-soluble Vitamins, Vol. 9, especially pages 128–133.

The process according to the invention is generally carried out in such a way that the dispersion containing the active substance is prepared by dissolving gelatin in hot water (at 50°–70° C.), adding to the solution the sugars, the amino compounds, the vitamins and/or carotenoids, stabilizers and the other conventional additives, with or without additional water, and dispersing the mixture by vigorous agitation at elevated temperature. For the thermal crosslinking of the powder which takes place in the last step, the dispersion should be at pH 4–10, which can be adjusted by adding bases such as NaOH, KOH, Ca(OH)$_2$, MgO, sodium carbonate or NH$_4$OH.

The subsequent processing of the dispersion to give the powders according to the invention can take place by all the processes known from the literature.

Because of the required particle size distribution of the powders (diameter from 0.1 to 0.6 mm), the preferred processes include measures to keep the gelled droplets of the dispersion separate from one another until the shape has stabilized.

Examples which may be mentioned are the process disclosed in EP-B1 74050 in which the dispersion is sprayed into hydrophobic silica or a metal salt of a higher fatty acid, or else the process disclosed in EP-B1 285 682 in which the dispersion is sprayed into starch powder. It has emerged that, especially in processes used for preparations with gelatin contents below 35% by weight, the spraying can very particularly advantageously be carried out with hydrophobic silica as dusting powder.

The powders produced by the described processes have, after drying, a water content of less than 10%, normally less than 6%. The products in powder form obtained in this way are composed of particles with a good surface structure. They rapidly dissolve in water at about 40° C. to give a milky dispersion.

The thermal curing of the dried powder is carried out at from 60° to 180° C., and the rate of the crosslinking which takes place increases as the temperature rises. The crosslinking is preferably carried out at from 70° to 130° C. over the course of from 5 minutes to 3 hours. The powders prepared in this way are insoluble in boiling water and have excellent stability, as is shown by the stability test on vitamin A acetate dry powder described hereinafter.

The process according to the invention can be used to prepare stable vitamin and/or carotenoid dry powders which are insoluble in hot water and which, despite the use of only about 20 to 35% by weight, based on the powder dry matter, of gelatin, compared with about 40 to 45% by weight in the prior art, have a stability which is at least as good.

Stability Test

A vitamin A acetate dry powder based on gelatin and lysine (cf. Example 3) according to the invention was compared with a vitamin A acetate dry powder containing only gelatin but prepared in the same way (cf. Comparative Example 4). Both dry powders were subjected to the premix stress test (40° C./70% relative humidity), which is described hereinafter, both as only dried (i.e. uncrosslinked) product and as product crosslinked by thermal treatment.

The premix had the following composition:

| Wheat bran | 60% |
|---|---|
| Choline chloride (50% on SiO$_2$) | 30% |
| Trace element mix | 10% |

The trace element mix was composed of:

| CuSO$_4$.5 H$_2$O | 37.43% |
|---|---|
| FeSO$_4$.7 H$_2$O | 46.78% |
| ZnO | 11.79% |
| MnO | 3.61% |
| CoCO$_3$ | 0.39% |

In each case 1 g of vitamin A dry powder was mixed into 99 g of the premix and then 4 g of this mixture were stored at 40° C. and 70% relative humidity, checking the vitamin A content at the start and after 4 weeks. The vitamin A contents after 4 weeks are shown in the following Table as a percentage of the initial contents.

A comparable indicator of the stability is the enzymatically detectable sugar content remaining after crosslinking. As the degree of crosslinking increases, the detectable sugar content of the powder decreases and, conversely, the stability increases. The residual sugar contents are therefore also indicated in the following Table. Other examples of the residual sugar content after crosslinking are given in the Examples.

|  | Dry powder of Ex. 3 | | Dry powder of Ex. 4 | |
|---|---|---|---|---|
|  | a) un-crosslinked | b) crosslinked | a) un-crosslinked | b) crosslinked |
| Retention after 4 weeks | 64% | 83% | 60% | 77% |
| Residual fructose | 9% | 3.6% | 9% | 6.4% |

The stability test shows that thermally crosslinked vitamin A dry powders are distinctly more stable than the uncrosslinked starting materials. Furthermore, the vitamin A dry powder according to the invention (Example 3 containing 25% gelatin and 2.5% lysine) is even more stable than the vitamin A dry powder of Comparative Example 4 (40% gelatin, 0% lysine).

Comparison of the stability data on dry powders in the previously described premix test also reveals a distinct increase in stability when the spray dispersion is adjusted with basic compounds to a higher pH. This is shown by comparison of following Examples 19 and 20.

EXAMPLE 1

85.2 g of gelatin A, Bloom 100, were added to 230 g of water and, after swelling for 30 minutes, dissolved by heating to 70° C. Addition of 42.8 g of fructose syrup (sugar content 70%, of which 95% fructose in dry matter) was followed by successive addition of 15 g of glycerol, 89.1 g of corn starch, 7.5 g of β-alanine and 75.3 g of vitamin A acetate (2.19 million IU/g, prepared from vitamin A acetate 2.9 million IU/g and stabilized with 100 mg of ethoxyquin and 14.5 mg of BHT per million IU of vitamin A). After addition of a further 170 g of water the mixture was emulsified by vigorous agitation at 60° C. The emulsion was sprayed at 55° C. and under from 5.5 to 6.5 bar through a single-component nozzle into a cloud of hydrophobic silica in a spray tower. The still moist product was dried in a fluidized bed dryer at room temperature to a residual moisture content of 5.2% and separated from the excess silica. The fructose content determined enzymatically was 9.0%. Subsequently 10 g of the resulting powder were heated in a rotating aluminum flask immersed in an oil bath at 120° C. for 20 minutes (min). The resulting brown powder had a vitamin A content of 560,300 IU/g and a residual moisture content of 2.1%. The residual fructose content was found to be 2.4%.

Alternatively, 10 g of the uncrosslinked powder were heated at 100° C. for 24 min. The resulting brown powder was not dispersible in boiling water (particles remained unchanged ).

EXAMPLES 2 TO 16

The procedure of Example 1 was used to prepare emulsions with the ingredients indicated in the following Table, followed by spraying to give a powder which was dried and then heated at 120° C. for 20 min. A vitamin A acetate containing 2.19 million IU/g which had been stabilized with 100 mg of ethoxyquin and 14.5 mg of BHT per million IU was used in all the experiments. Gelatin A Bloom 100 was used in all the Examples. The fructose syrup employed in the Examples was the fructose syrup described in detail in Example 1.

The gelatin contents stated in the following Table are percentages of the weight of the dried powder. They were calculated taking account of the water contents in the auxiliaries ( gelatin 12%; corn starch 13%, sugar 30%) and of the residual water content and of the dusting with silica, which together amount to about 7% by weight.

TABLE 1

| | Ingredients of the emulsion | | | | | | | | | Heat-treated product | | | |
|---|---|---|---|---|---|---|---|---|---|---|---|---|---|
| Ex. | Vit. A [g] | Sugar [g] | Gelatin [g (%)] | Amino compound [g] | Corn starch [g] | Water [g] | Glycerol [g] | Arachis oil [g] | Sodium phytate [g] | Residual moisture [%] | Residual fructose [%] | Vit. A content [IU/g] | Time[5] 100/ 110° C. [min] |
| 2 | 75.3 | 42.8 fructose syrup | 85.2 (25) | 7.5 Ca β alaninate | 89.1 | 400 | 15 | — | — | 2 | 0.3 | 562,400 | 6/ |
| 3 | 75.5 | 42.8 fructose syrup | 85.2 (25) | 7.5 lysine | 103 | 350 | — | — | — | 2.5 | 3.7 | 577,400 | 39/10 |
| 4 comp. | 75.3 | 42.8 fructose syrup | 136.4 (40) | — | 60 | 400 | — | — | — | 2.3 | 6.4 | 568,900 | >60/40 |
| 5 | 75.6 | 42.3 invert sugar[3] | 85.2 (25) | 7.5 lysine | 66.2 | 350 | 15 | 15[1] | 3[2] | 3.9 | | 549,500 | |
| 6 | 75.6 | 42.3 invert sugar[3] | 85.2 (25) | 9.6 L-lysine.HCl | 63.8 | 350 | 15 | 15[1] | 3[2] | 3.1 | | 551,000 | |
| 7[4] | 50.2 | 28.6 fructose syrup | 56.8 (25) | 7.5 L-lysine.HCl | 45.6 | 250 | 10 | 10[1] | 2.4[2] | 2.7 | | 603,000 | 25/ |
| 8 | 75.3 | 64.2 fructose syrup | 85.2 (25) | 15 L-lysine | 77.3 | 350 | — | — | — | 2.2 | 3.7 | 554,600 | 10/ |
| 9 | 75.3 | 85.6 fructose syrup | 85.2 (25) | 30 L-lysine | 42.7 | 400 | — | — | — | 5.2 | 1.7 | 562,600 | 8/ |
| 10 | 100.4 | 112.7 invert sugar[3] | 68.2 (15) | 4.0 Ca β-alaninate | 123 | 400 | 20 | — | — | 3.3 | 6.7 | 553,000 | 30/ |
| 11 | 100.4 | 112.7 invert sugar[3] | 68.2 (15) | 20.0 Ca β-alaninate | 104 | 400 | 20 | — | — | 3.8 | 3.0 | 563,700 | 11/ |
| 12 | 75.3 | 42.8 fructose syrup | 85.2 (25) | 7.5 glycine | 89.1 | 400 | 15 | — | — | 2.7 | 2.8 | 525,400 | |

TABLE 1-continued

| | Ingredients of the emulsion | | | | | | | | Heat-treated product | | | |
|---|---|---|---|---|---|---|---|---|---|---|---|---|
| Ex. | Vit. A [g] | Sugar [g] | Gelatin [g (%)] | Amino compound [g] | Corn starch [g] | Water [g] | Glycerol [g] | Arachis oil [g] | Sodium phytate [g] | Residual moisture [%] | Residual fructose [%] | Vit. A content [IU/g] | Time[5] 100/110° C. [min] |
| 13 | 75.3 | 42.8 fructose syrup | 85.2 (25) | 7.5 L-α-alanine | 103 | 350 | — | — | — | 2.5 | 4.5 | 538,600 | 30/ |
| 14 | 75.3 | 42.8 fructose syrup | 85.2 (25) | 7.5 DL-methionine | 89.1 | 410 | 15 | — | — | 2.5 | 4.5 | 570,300 | 30/ |
| 15 | 75.3 | 42.8 fructose syrup | 85.2 (25) | 7.5 hexamethylenediamine | 103 | 350 | — | — | — | 1.7 | 2.2 | 563,000 | 9/ |
| 16 | 100 | 84.5 invert sugar[3] | 90.9 (20) | 6.0 3-aminopropanol | 120.7 | 400 | 20 | — | — | 3.2 | | 574,200 | 28/8 |

[1]Arachis oil was added immediately before additon of the vitamin A acetate.
[2]Sodium phytate was added immediately after addition of the corn starch.
[3]Proprietary name Isosweet supplied by Amylum, sugar content 70%, of which 51% dextrose and 42% fructose in dry matter.
[4]Before adding the vitamin A acetate, the mixture with all the other ingredients was adjusted to pH 8.7 with 25% strength NaOH.
[5]Minimum crosslinking time at which the product heated at 100 or 110° C. no longer forms a dispersion in boiling water.

EXAMPLE 17

The procedure of Example 1 was used to prepare an emulsion with the ingredients detailed below, followed by spraying to give a powder and drying.

| | |
|---|---|
| Vitamin A acetate 2.19 million IU/g stabilized with 100 mg of ethoxyquin and 14.5 mg of BHT per million IU | 52.4 g |
| Vitamin D3 40 million IU/g (dissolved in vitamin A acetate) | 0.55 g |
| Fructose syrup | 29.8 g |
| Gelatin A Bloom 100 | 59.3 g |
| Ca β-alaninate | 5.2 g |
| Corn starch | 72.0 g |
| Water | 280.0 g |

The resulting product was heated at 120° C. for 20 min. The residual moisture content was 4.1%, the residual fructose content was 2.4%, the vitamin A content was 558,200 IU/g and the vitamin D3 content was 109,000 IU/g.

EXAMPLE 18

The procedure of Example 1 was used to prepare a canthaxanthin dispersion with the ingredients detailed below, followed by spraying to give a powder and drying.

| | |
|---|---|
| Canthaxanthin micronized | 37.0 g |
| Ethoxyquin | 11.0 g |
| Ascorbyl palmitate | 3.0 g |
| Gelatin B Bloom 200 | 94.3 g |
| Invert sugar[3] | 224.3 g |
| Ca β-alaninate | 17.0 g |
| Water | 613.0 g |

The residual moisture content of the resulting powder was 7%. The enzymatically determined fructose content was 16.0% and the glucose content was 20.8%.

The powder was heated at 120° C. for 20 min. The residual moisture content of the heated product was 4.2%, and the residual fructose and glucose was found to be 11% and 4.6%. The canthaxanthin content of the powder was 12.2%.

EXAMPLES 19-21

99.9 g of gelatin A Bloom 100 were added to 230 g of water and, after swelling for 30 minutes, dissolved by heating to 70° C. Addition of 61.9 g of invert sugar (proprietary name Isosweet supplied by Amylum, sugar content 70%, of which 51% dextrose and 42% fructose in dry matter) was followed by successive addition of the amounts, indicated in Table 2, of glycerol, corn starch and vitamin A acetate (2.19 million IU/g, prepared from vitamin A acetate 2.9 million IU/g and stabilized with 100 mg of ethoxyquin and 14.5 mg of BHT per million IU of vitamin A). After addition of a further 140 g of water and the amount, which is evident from Table 2, of a 10% strength aqueous NaOH solution, the mixture was adjusted to the pH indicated in Table 2 and emulsified by stirring vigorously at 60° C.

The emulsion was sprayed at 55° C. and under from 5.5 to 6.5 bar through a single-component nozzle into a cloud of hydrophobic silica in a spray tower. The still moist product was dried in a fluidized bed dryer at room temperature to a residue of moisture content of 5.2% and separated from the excess silica. Subsequently 10 g of the resulting powder were heated in a rotating aluminum flask immersed in an oil bath at 110° C. for the time indicated in Table 2 (minimum crosslinking time after which the product heated at 110° C. no longer disperses in boiling water ).

The resulting products were subjected to the premix stress test (40° C./70% relative humidity), which is described hereinbefore, for six weeks and then tested for their vitamin A content.

Comparison of the results for Examples 19 and 21 with the Comparative Example 20 (without addition of base to the emulsion) shows that a distinct increase in stability of the product, and a reduction in the minimum crosslinking time, can be achieved by increasing the pH of the spray emulsion with NaOH.

c) thermally curing the powder at from 60° to 180° C.,

TABLE 2

| | Ingredients of the emulsion | | | | | | Heat-treated product | | |
|---|---|---|---|---|---|---|---|---|---|
| Ex. | Vit. A [g] | Sugar [g] | Gelatin [g (%)] | NaOH [g (pH)] | Corn starch [g] | Water [g] | Glycerol [g] | Vit. A content [IU/g] | Time at 110° C. | Retention after 6 weeks |
| 19 | 75.3 | 61.9 | 99.9 (30) | 13(8) | 57.9 | 370 | 14.6 | 571.800 | 18 | 80.7 |
| 20* | 75.3 | 61.9 | 99.9 (30) | —(5.3) | 74.9 | 370 | — | 576.000 | 45 | 74 |
| 21 | 75.3 | 61.9 | 99.9 (30) | 19 (9.0) | 74.9 | 370 | — | 558.200 | 26 | 83 |

*Comparative Example

EXAMPLE 22

In the same way as described for Examples 19 to 21, an emulsion was prepared with the composition indicated for Comparative Example 20 and consequently portions were adjusted to the pH evident from Table 3 using the base evident from Table 3, and the minimum crosslinking time at 120° C. was determined for the dry powders prepared as in Examples 19-21.

TABLE 3

| Composition of the emulsion | Added base | pH of the spray emulsion | Minimum crosslinking time at 120° C. [min] |
|---|---|---|---|
| a) as Example 20 | — | 5.3 | 26 |
| b) as Example 20 | NaOH | 9.0 | 11 |
| c) as Example 20 | KOH | 9.0 | 10 |
| d) as Example 20 | MgO | 9.0 | 14 |
| e) as Example 20 | Ca(OH)$_2$ | 9.0 | 11 |

Increasing the pH of the emulsion with various bases before the spraying leads to a markedly reduced minimum crosslinking time for the dry powders.

We claim:

1. A process for preparing stable dry powders which are insoluble in hot water and which contain one or more fat-soluble vitamins and/or one or more carotenoids, which comprises the following steps:
   a) preparing an aqueous dispersion containing essentially these fat-soluble active substances, film-forming colloids and reducing sugars,
   b) converting this dispersion into dry vitamin and/or carotenoid products in powder form and
   c) thermally curing the powder at from 60° to 180° C., wherein gelatin in amounts of from 20 to 35% of the weight of the powder dry matter, in combination with one or more physiologically tolerated amino compounds which are free or bonded in the manner of a salt and which contain a basic primary amino group and, in addition, either another amino group, a hydroxyl group, an alkoxy group or a carboxyl group, and/or in combination with sufficient basic alkali metal or alkaline earth metal compound for the dispersion to have a pH of from 7.5 to 10.

2. A process as claimed in claim 1, wherein gelatin is used in amounts of from 20 to 35% of the weight of the powder dry matter, in combination with from 0.3 to 20% by weight, based on the powder dry matter, of the amino compound or compounds which is/are free or bonded in the manner of a salt, the total of the amount of gelatin and the amount of amino compound not exceeding 45% by weight, as film-forming colloid.

3. A process as claimed in claim 1, wherein gelatin in combination with lysine or β-alanine or one of their salts is used as film-forming colloid.

4. A process as claimed in claim 1, wherein gelatin in combination with calcium β-alaninate is used as film-forming colloid.

5. A process as claimed in claim 1, wherein gelatin in combination with sufficient alkali metal or alkaline earth metal hydroxide for a dispersion to have a pH of from 8 to 9.5 is used as film-forming colloid.

6. The process of claim 7 wherein, in step b) of the process, the dispersion is converrted into dry viatmin and/or carotenoid products in powder form by spraying into hydrophobic silica or a metal salt of a higher fatty acid.

* * * * *

UNITED STATES PATENT AND TRADEMARK OFFICE
CERTIFICATE OF CORRECTION

PATENT NO.: 5,356,636

DATED: October 18, 1994

INVENTOR(S): SCHNEIDER et al.

It is certified that error appears in the above-identified patent and that said Letters Patent is hereby corrected as shown below:

Claim 6, column 12, line 45:
 "viatmin" should read -- vitamin --.

Signed and Sealed this

Thirteenth Day of December, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,356,636

DATED : October 18, 1994

INVENTOR(S) : Schneider et al

It is certified that error appears in the above-indentified patent and that said Letters Patent is hereby corrected as shown below:

Column 12, claim 6, line 1, delete "claim 7" and substitute --claim 1--.

Signed and Sealed this

Twenty-second Day of August, 1995

Attest:

BRUCE LEHMAN

Attesting Officer

Commissioner of Patents and Trademarks